United States Patent [19]

Goldberg et al.

[11] 4,452,254

[45] Jun. 5, 1984

[54] CARDIAC ELECTRODE AND METHOD FOR INSTALLING SAME

[76] Inventors: Edward M. Goldberg, 225 Maple Hill Rd., Glencoe, Ill. 60022; Seymour Bazell, 9235 N. Latrobe, Skokie, Ill. 60077

[21] Appl. No.: 282,750

[22] Filed: Jul. 13, 1981

[51] Int. Cl.³ .............................................. A61N 1/36
[52] U.S. Cl. .................................................. 128/785
[58] Field of Search .................... 128/419 P, 784, 785, 128/786

[56] References Cited

U.S. PATENT DOCUMENTS

| | | | |
|---|---|---|---|
| 3,416,534 | 12/1968 | Quinn | 128/785 |
| 3,472,234 | 10/1969 | Tachick | 128/785 |
| 3,835,864 | 9/1974 | Rasor et al. | 128/785 |
| 3,844,292 | 10/1974 | Bolduc | 128/785 |
| 4,026,303 | 5/1977 | Bakotai | 128/785 |
| 4,207,903 | 6/1980 | O'Neill | 128/785 |
| 4,287,896 | 9/1981 | Grigorov et al. | 128/786 |

FOREIGN PATENT DOCUMENTS

| | | | |
|---|---|---|---|
| 4967 | 10/1979 | European Pat. Off. | 128/785 |
| 35959 | 9/1981 | European Pat. Off. | 128/785 |
| 2806069 | 8/1979 | Fed. Rep. of Germany | 128/785 |

Primary Examiner—William E. Kamm
Assistant Examiner—Mitchell J. Shein
Attorney, Agent, or Firm—Norman Lettvin

[57] ABSTRACT

A novel cardiac lead assembly is described which includes an elongatable coil spring which serves to connect a screw-in electrode tip with a connector. A flange is affixed to the electrode tip and the lead is positioned inside a tubular lead insertion device. In order to install this lead in a heart, the coil spring is stretched while using the installation device to position the flange precisely with respect to the heart. Once proper position of the electrode tip has been assured, the coil spring is released abruptly such that the potential energy of the spring propels the electrode tip against the heart with sufficient momentum to embed the electrode tip in the heart in a single motion. Preferably, the spring also imparts an angular momentum to the electrode tip which tends to screw the electrode tip into the heart. The illustrated embodiments of the lead include a plurality of spirally oriented elongated prongs which serve to engage the surface of the heart mechanically. Also, a braided wire sheath is disclosed which is rigidly attached to the flange at its distal end and serves to transmit torques down the length of the lead efficiently for screwing the lead into or out of the heart as desired.

38 Claims, 6 Drawing Figures

U.S. Patent   Jun. 5, 1984   4,452,254
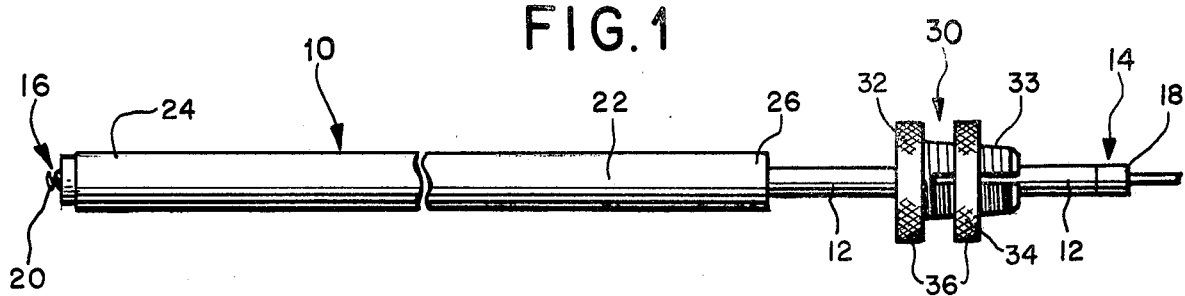
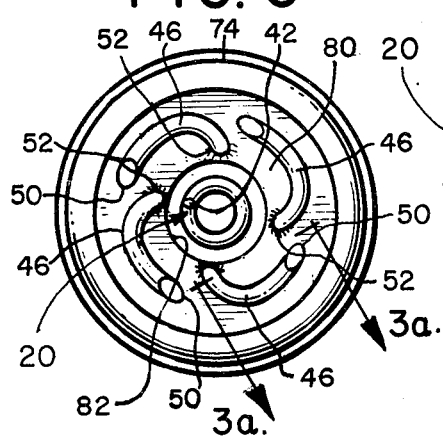
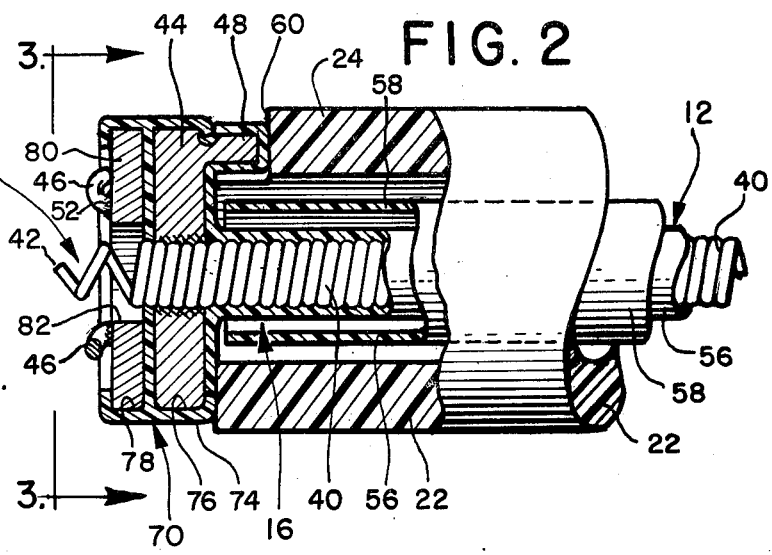
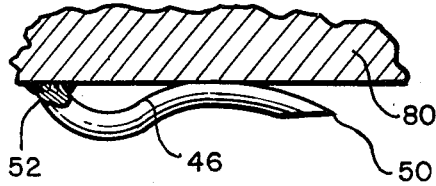
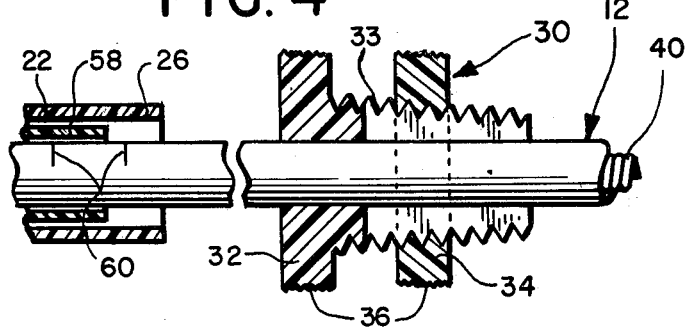
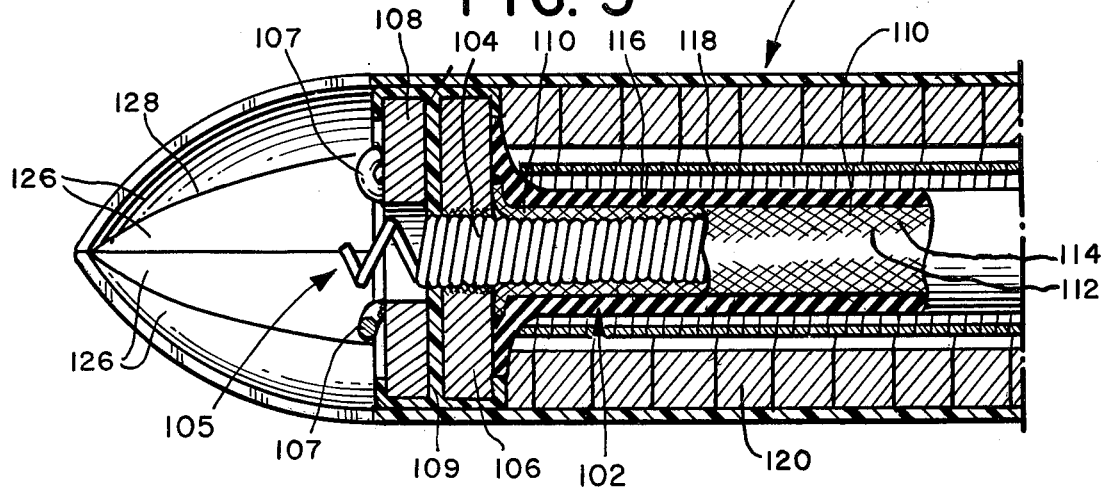

CARDIAC ELECTRODE AND METHOD FOR INSTALLING SAME

BACKGROUND OF THE INVENTION

This invention relates to electrical cardiac leads of the type used to transmit electrical signals from a pacemaker to the heart of a living subject, and in particular to improvements in such leads and their method of installation which allow more accurate installation with reduced damage to the tissue of the heart.

For some time, electrical leads have been used to conduct pacing signals from a pacemaker to the heart of a living subject. Such cardiac electrodes typically terminate in an electrode tip which must be surgically implanted in the heart to deliver the desired pacing signals to an appropriate portion of the heart. Screw-in electrodes can be implanted in the heart with relatively little trauma to the heart muscle. However, even with screw-in electrodes, accurate manual implantation can be difficult due to movement of the heart, and this movement can result in undesired laceration of the heart by the electrode before the electrode has become embedded in the heart.

Lacerations of the type described above can result in the formation of undesirable scar tissue near or immediately adjacent to the electrode. Such scar tissue tends to increase the voltage of the pacing signal required to pace the heart properly. This increased voltage in turn reduces the life of batteries used to power the associated pacemaker.

In addition, many commonly used screw-in electrodes use perforated, fabric skirts near the screw-in electrode as an aid in fastening the electrode to the heart. In use, these fabric skirts serve as bonding sites at which heart tissues can engage the electrode to hold the electrode firmly to the heart. Such bonding skirts present important disadvantages in that they do not significantly help to secure the electrode to the heart for some period of time after the electrode has been implanted in the heart. This is because heart tissues do not grow into and around the fabric skirt until a period of time ranging from several days to weeks has elapsed. During this period of time, prior to the attachment of the skirt to the heart, it is the screw-in electrode itself which holds the electrode in place.

Once fabric skirts of the type described above have become embedded in heart tissue, the electrode often cannot be removed from the heart without cutting the skirt and associated heart tissue from the heart. Thus, the removal of the electrode is a surgical procedure which serves further to traumatize the heart and can result in the formation of additional scar tissue.

Many conventional screw-in electrodes have electrodes approximately six millimeters in length. However, it has been established that the wall thickness of the muscle layer of the apex of the left ventricle of many human subjects is at its thinnest point less than two millimeters in thickness. Thus, there is a very real danger that screw-in electrodes of the conventional type may perforate the ventricular wall. See, for example, the discussion of this problem published in Vol. 39 of the *British Heart Journal* at pages 806–809 (1977).

SUMMARY OF THE INVENTION

The present invention is directed to improved epicardial and endocardial leads and to methods for installing such leads which substantially reduce the problems discussed above.

According to the method of this invention, a cardiac lead assembly is provided which comprises a cardiac lead, an electrode tip included in the lead, and a lead insertion device. This cardiac lead is attached to a heart by first pointing the electrode tip of the cardiac lead assembly at a selected portion of a heart, and then accelerating the electrode tip toward the heart and away from the lead insertion device with sufficient momentum to cause the electrode tip to penetrate a surface of the heart and become embedded therein. When the electrode tip is of the screw-in type, it is sometimes preferable to accelerate the tip toward the heart with an angular momentum which tends to cause the screw-in tip to screw itself into the heart muscle. Preferably, the improved method of this invention is practiced with a cardiac lead assembly which comprises an electrical lead, an electrode tip positioned to extend away from one end of the lead, and means for accelerating the electrode tip in the direction of the heart with sufficient momentum to cause the electrode tip to penetrate a surface of the heart, thereby embedding the electrode tip in the heart. The methods and leads of this invention can be used in connection with both endocardial and epicardial leads.

In the preferred embodiments described below, the electrical lead comprises a helical spring conductor which acts both to conduct pacing signals to the electrode tip and to serve as a biasing member. In this preferred embodiment the accelerating means comprises a tubular structure positioned around the lead such that when the coiled conductor is stretched and then released, the electrode tip is caused to accelerate towards the heart muscle. Preferably, the lead is provided with a flange secured adjacent the electrode tip such that the tip extends away from the flange, and at least one elongated prong is positioned on the flange adjacent the electrode tip to penetrate and mechanically engage the heart, thereby securing the flange to the heart. Additionally, some embodiments of the lead of this invention are preferably provided with a braided wire outer sheath which efficiently transmits torque down the lead to the electrode tip. This outer wire sheath can be used to rotate the electrode tip either to embed the tip more firmly in the heart or, alternately, to unscrew the tip from the heart, thereby removing the screw-in electrode from the heart with a minimum of damage to the tissues of the heart.

The method and apparatus of this invention provide a number of significant advantages. Since the electrode tip is installed quickly in a single, sudden motion, the electrode can be installed accurately in the desired portion of the heart with reduced damage to the heart due to relative movement between the heart and the electrode tip during insertion of the electrode tip. In this way scarring of the heart is reduced, as is the resulting pacing threshold for the electrode. As explained above, this allows an increase in the life of batteries used to power the associated pacemaker.

Moreover, the preferred embodiments of the lead of this invention provide an excellent purchase for the electrode tip in the heart muscle because the prongs of the flange serve to engage the heart muscle mechanically from the time the electrode is embedded in the heart. Since the prongs of the flange serve to secure the electrode to the heart reliably, the length of the central screw-in coil can be reduced, thereby reducing the probability that the screw-in electrode will perforate the wall of the heart. Furthermore, since no fabric skirts are used in the preferred embodiment, it can readily be removed from the heart when necessary without cutting the electrode out of the heart.

The invention itself, together with further objects and attendant advantages, will best be understood by reference to the following detailed description taken in connection with the accompanying drawings.

BRIEF DESCRIPTION OF THE DRAWINGS

FIG. 1 is an overall view of a first preferred embodiment of an epicardial lead assembly suitable for practicing a preferred embodiment of the method of this invention.

FIG. 2 is an enlarged sectional view of the distal end of the lead assembly of FIG. 1.

FIG. 3 is an end view taken along line 3—3 of FIG. 2.

FIG. 3a is an enlarged sectional view taken along line 3a—3a of FIG. 3.

FIG. 4 is an enlarged sectional view of the removable handle of the lead assembly of FIG. 1.

FIG. 5 is an enlarged sectional view of the distal end of a second preferred embodiment of an endocardial lead assembly of this invention.

DETAILED DESCRIPTION OF THE PRESENTLY PREFERRED EMBODIMENTS

Turning now to the drawings, FIG. 1 shows an overall view of an epicardial lead assembly 10 which embodies several features of the present invention and can be used to practice the method of this invention. This lead assembly 10 includes an elongated flexible lead 12 which defines a proximal end 14 and a distal end 16. In this embodiment the proximal end 14 defines an electrical connector adapted to interconnect the lead 12 with a pacemaker (not shown). The distal end 16 of the lead 12 defines an electrode tip, which in this preferred embodiment is a screw-in electrode tip 20.

The lead assembly 10 also includes a tubular lead insertion device 22. In this embodiment the lead insertion device 22 comprises a hollow, elongated, substantially rigid tube which defines a distal end 24 adjacent the distal end 16 of the lead 12 and a proximal end 26. This tube may be formed of any suitably rigid material, such as a high impact styrene or a metal. Also included in the lead assembly 10 is a removable handle 30 which is releasably secured to the lead 12 adjacent the proximal end 26 of the insertion device 22.

Turning now to FIG. 2, the distal end 16 of the lead 12 and the insertion device 22 are there shown in greater detail. As shown in FIG. 2, the lead 12 includes a closed coil spring 40 includes a distal end 42 which defines 1-½ or 2 spread coils which serve to form the screw-in electrode tip 20. Platinum or gold electrode surfaces (not shown) can be bonded to or plated on the electrode tip 20. The coil spring 40 extends away from the screw-in electrode tip 20, and serves as a flexible electrical conductor, electrically connecting the connector 18 with the screw-in electrode tip 20. In this preferred embodient, the coil spring 40 is formed of type 302, 304 or 416 stainless steel, having a tensile strength of about 280-300 kpsi. Preferably the spring has an outside diameter of 0.054 inches and is formed of wire 0.012 inches in diameter. A thin, circular, stainless steel flange 44 is securely mounted to the coil spring 40 adjacent the electrode tip 20, as for example by welding the flange 44 to the coil spring 40. The flange 44 serves as a mounting surface for an insulating bracket 70. This bracket 70 is a flanged disc having a central opening 72, and is formed of a suitable insulating material such as teflon, for example. A peripheral flange 74 extends around the bracket 70 to define first and second recesses 76,78 on respective sides of the bracket 70. The recess 76 is sized to receive the flange 44 such that the distal face of the flange 44 is surrounded and the bracket 70 is locked against rotation with respect to the flange 44. The recess 78 is sized to receive a stainless steel disc 80 which is secured to the bracket 70 by the peripheral flange 74. The disc 80 defines a central opening 82 which is larger than the electrode tip 20 such that the disc 80 is electrically insulated from the electrode tip 20. Preferably the peripheral flange 74 is peened in place to mount the bracket 70 securely on the flange 44 and the disc 80 securely on the bracket 70. A plurality of elongated prongs 46 are mounted on the surface of the disc 80 opposed to the bracket 70 such that the prongs 46 are electrically insulated from the flange 44. Each of these prongs 46 should preferably be formed of a flexible, stainless spring steel welded to the disc 80. Alternately, the prongs 46 can be stamped out of the disc 80, or may be mounted directly to an insulating flange so as to insulate the prongs 46 from the electrode tip 20. In addition, one or more keys 48 are mounted on the flange 44 so as to extend away from the bracket 70.

As best shown in FIG. 3 the elongated prongs 46 are each provided with a respective sharpened end 50 and an anchor end 52. Each of the sharpened ends 50 is adapted to pierce the heart muscle, and each of the anchor ends 52 serves to attach the respective prong 46 to the disc 80 by capturing tissue between the prong 46 and the disc 80. As shown in FIG. 3, each of the prongs 46 is arranged in a spiral pattern such that each respective sharpened end 50 is situated at a greater radial distance from the electrode tip 20 than is the respective anchor end 52. The prongs 46 are shaped and positioned such that when the flange 44 is rotated in the appropriate direction against a surface of a heart, each of the prongs 46 penetrates the heart to mechanically engage the disc 80 and the flange 44, and therefore the electrode tip 20, in the muscle of the heart.

Returning to FIG. 2, the lead 12 also includes an insulating sheath 56 which is disposed over the coil spring 40 and the exposed portions of the flange 44 so as to electrically isolate the electrode tip 20. Preferably, this sheath 56 is formed of an impermeable, elongatable, biocompatible material such as medical grade silicone or urethane. Disposed around the insulating sheath 56 is a tubular liner 58. This liner can, for example, be made of coiled flat wire or a plastic tube formed of a low friction material such as teflon. The liner 58 is slidably mounted over the insulating sheath 56 such that the liner 58 can be readily removed from the lead 12 when desired. The liner 58 can be split longitudinally to facilitate its removal from the lead 12.

As previously explained, the lead assembly 10 includes a tubular lead insertion device 22 which is disposed around the lead 12. As shown in FIG. 2, this lead insertion device 22 defines a keyway 60 at its distal end 24. This keyway 60 is shaped to mate with the key 48 in order to lock the flange 44 against rotation with respect to the insertion device 22. Thus, the keyway 60 cooperates with the key 48 to transmit torque from the insertion device 22 to the flange 44, and thereby to the electrode tip 20. As shown in FIG. 2 the insertion device 22 fits loosely over the liner 58 such that the liner 58 and therefore the lead 12 are free to slide within the insertion device 22. Preferably, the edges of the keyway 60 are rounded so as to minimize damage to the insulating sheath 56 over the key 48.

Turning now to FIG. 4, the handle 30 comprises a split ring chuck 32 which defines a threaded end section 33. This split ring chuck 32 defines a plurality of splits or grooves (not shown) which extend longitudinally along the threaded end section 33. The handle 30 also includes a nut 34 adapted to mate with the threaded end section 33. The threaded end section 33 is shaped such that the handle 30 can be securely clamped to the lead 12 merely by tightening the nut 34 on the split ring chuck 32. Both the chuck 32 and the nut 34 define respective knurled outer edges 36 which provide a secure gripping surface for the handle 30. The handle 30 is removably attached to the lead 12, and the handle 30 can be readily removed from the lead 12 merely by separating the nut 34 from the split ring chuck 32, and then sliding the pieces of the handle 30 over the proximal end 14 of the lead 12.

The components of the lead 12 cooperate to provide a flexible, elongatable lead. As previously mentioned, the coil spring 40 preferably is formed of a spring steel, and the insulating sheath 56 is preferably formed of an extensible, flexible elastomeric material such as silicone rubber. Preferably, the flange 44 and the coil spring 40 are insulated by the sheath 56 and the prongs 46 are insulated from the flange 44 such that the only electrical contact between the coil spring 40 and the heart muscle is by means of the screw-in electrode tip 20.

Having described the structure of the lead assembly 10 of FIGS. 1-4, its operation can now be discussed. In use, the lead assembly 10 is used to embed the screw-in electrode tip 20 in a heart through a novel procedure which results in accurate placement of the electrode tip 20 in the desired portion of the heart, as well as reduced laceration and scarring of the heart muscle itself. The first step in installing the electrode tip 20 in the heart is to gain access to the exterior surface of the heart in the conventional manner, and then to locate the position on the surface of the heart at which it is desired to embed the screw-in electrode tip 20. These steps are known to those skilled in the art and therefore will not be described in detail here. One access to the heart has been gained, the surgeon grasps the lead insertion device 22 near its distal end 24 and points the screw-in electrode tip 20 at the selected portion of the heart. Then the surgeon grasps the handle 30 and elongates the lead 12 inside the lead insertion device 22 by stretching the coil spring 40 and insulating sheath 56. Preferably, the surgeon rotates the handle 30 as he elongates the lead 12 so as to twist as well as elongate the coil spring 40. The direction of rotation of the handle 30 should be chosen such that the spring will tend to rotate the electrode tip 20 in the direction which tends to screw the electrode tip 20 into the heart. Because the key 48 mates with the keyway 60, the lead insertion device 22 substantially locks the flange 44 against rotation as the handle 30 is being rotated and withdrawn. Preferably, the lead 12 is provided with one or more markings 62 which assist the surgeon in visually gauging the extent to which the lead 12 has been elongated.

Once the handle 30 has been moved away from the proximal end 26 of the lead insertion device 22, the surgeon then reconfirms that the electrode tip 20 is pointed at the selected portion of the heart. Once the lead 12 has been stretched and twisted to an appropriate extent and the electrode tip 20 has been properly positioned, the surgeon then abruptly releases the handle 30 while securely holding the distal end 24 of the lead insertion device 22 in place adjacent the heart. Once the handle 30 is released the coil spring 40 snaps the handle 30 towards the proximal end 26 of the lead insertion device 22 and imparts a momentum to the electrode tip 20 sufficient to embed the electrode tip 20 in the heart muscle. Preferably, the coil spring 40 also imparts an angular momentum to the electrode tip 20 which causes the electrode tip 20 to rotate in a direction which tends to screw the electrode tip 20 into the heart. As the lead 12 is moving inside the lead insertion device 22, the liner 58 serves to provide a low friction contact between the lead 12 and the interior surface of the lead insertion device 22, thereby facilitating movement of the lead 12. The spring constant and the degree of stretching of the lead 12 should be chosen such that the electrode tip 20 is accelerated toward the heart with sufficient momentum to embed the electrode tip 20 at least partially in the heart without excessively damaging or bruising the heart.

Once the handle 30 has been withdrawn and released and the spring action of the lead 12 has caused the electrode tip 20 to become embedded in the heart, the lead 12 can be further secured to the heart by engaging the key 48 in the keyway 60 and then manually rotating the lead insertion device 22 in such a manner as to cause the prongs 46 to penetrate and mechanically engage the heart muscle. Because of the spiral arrangement of the prongs 46, this final rotation of the flange 44 causes heart muscle to be pinched around the electrode tip 22, thereby reducing the prospects of blood leakage or hemorrhage around the electrode tip 20.

Because the prongs 46 serve to provide an immediate and reliable mechanical engagement between the flange 44 and the heart muscle, the length of the electrode tip 20 can be shortened. In this preferred embodiment, the length of the screw-in electrode tip 20 is in the range of 1-½ to 2 millimeters. In addition, the prongs 46 provide secure attachment for the flange 44 from the very start, and there is no need to wait for the growth of heart tissue through a permeable skirt to complete the attachment of the lead 12 to the heart. A further advantage of the lead of FIG. 1 is that since the only attachments between the flange 44 and the heart are made by the screw-in electrode tip 20 and the screw-in prongs 46, the entire lead can be removed from the heart when desired without cutting away portions of the heart muscle. The lead of FIG. 1 may be removed from the heart at any time merely by engaging a device such as the insertion device 22 on the key 48 and then rotating the flange 44 in such a manner as to unscrew both the electrode tip 20 and the prongs 46 from the heart. Thus, the illustrated lead of FIG. 1 is particularly suited for use with patients for whom it is important to minimize the formation of scar tissue on the heart muscle itself.

Once the lead 12 has been firmly placed in the heart, the lead assembly 10 is then disassembled. This is done by unscrewing the nut 34 from the split ring chuck 32 and then sliding the entire handle 30 over the proximal end 14 of the lead 12. Once the handle 30 has been removed, the lead insertion device 12 is then removed by sliding it over the proximal end 14 of the lead 12. In this preferred embodiment, the liner 58 is also removed from the lead 12 in the same manner. Once the lead assembly 10 has been disassembled, only the lead 12 remains connected to the heart. This lead 12 is then coupled to a pacemaker (not shown) in the conventional manner. If necessary, the connector 18 can be installed on the lead 12 after the insertion device 22 and the liner 58 have been removed in order to facilitate disassembly of the lead assembly 10.

The lead illustrated in FIGS. 1–4 provides a number of significant advantages. First, since the lead is embedded in the heart with a spring action provided by the coil spring 40, the electrode tip 20 can be precisely positioned in a moving heart. Furthermore, since the electrode tip 20 is embedded in a single motion, laceration of the heart muscle due to relative movement between the heart and the electrode tip during insertion is minimized. In this way the formation of scar tissue associated with lead insertion (and therefore undesirable elevations in pacing thresholds) is minimized. Furthermore, as explained above, the lead 12 is provided with a key 48 which can be used both to complete the embedding of the prongs 46 in the heart, as well as to unscrew the lead 12 from the heart in order to remove the lead 12 with a minimun of additional scarring of the heart itself.

Turning now to FIG. 5, many of the important features of this invention are not limited to use with epicardial leads, but can also be adapted for use with endocardial leads. FIG. 5 shows a preferred embodiment of one such endocardial lead. As shown in FIG. 5 this lead is part of a lead assembly 100 which comprises a cardiac lead 102 and a lead insertion device 120. This lead 102 is in many respects similar to the lead 12 previously described in connection with FIGS. 1–4. For example, this lead 102 includes a centrally disposed coil spring 104 which defines at its distal end with a screw-in electrode tip 105. The coil spring 104 is rigidly attached to a circular flange 106, as for example by welding the coil spring 104 to the flange 106. The flange 106 serves as a mounting surface for an insulating bracket 109, which in turn serves to mount a disc 108 on which are affixed a plurality of elongated prongs 107. Each of these elements of the lead 102 is comparable to the corresponding elements of the lead 12, and will not therefore be described in detail here.

One important difference between the lead 102 of FIG. 5 and the lead 12 of FIG. 1 is that the lead 102 includes a wire braid sheath 110 which extends along the length of the lead 102. This braid sheath 110 comprises a first plurality of elongated, flexible, stainless steel, wire filaments 112 arranged in a helical pattern over the coil spring 104, and a second plurality of elongated, flexible, stainless steel, wire filaments 114 arranged in a helical pattern over the coil spring 104 with a reverse twist with respect to the first plurality of filaments 112 such that the first plurality of filaments 112 repeatedly crosses the second plurality of filaments 114. The distal ends of the filaments 112,114 are rigidly affixed to the flange 106, as for example by welding or silver soldering them to the flange 106. Only the distal portion of the lead 102 is shown in FIG. 5; however, the wire braid sheath 110 in this embodiment extends along the length of the lead 102 to a point adjacent its proximal end (not shown).

As will be explained below, the braid sheath 110 acts as a torque transmission structure which transmits torques applied to the proximal end of the braid sheath 110 efficiently to the flange 106, while maintaining a flexible lead. An elongatable insulation sheath 116 (similar to the sheath 56) is disposed over the braid sheath 110. This insulating sheath 116 is in turn covered by a flexible liner 118 formed of a helical coil of a low friction material, such as teflon or metal.

As previously explained, the lead assembly 100 includes a lead insertion device 120. In this embodiment the lead insertion device 120 is a flexible, tubular structure formed of a closely packed stainless steel wire coil. This insertion device 120 is sized to fit loosely over the liner 128 such that the lead 102 and the liner 118 are free to slide within the lead insertion device 120.

The lead assembly 100 also includes a resilient tip shield 124 which extends substantially over the electrode tip 105 as well as the lead insertion device 120. This tip shield 124 is a flexible, elastomeric tubular structure which defines at its distal end a plurality of segments 126 separated by slits 128. The tip shield can be formed of a material such as polyurethane. In the rest state, these segments 124 orient themselves as shown in FIG. 5 to cover the tip 105. However, the slits 128 are provided to allow the flange 106 and electrode tip 105 to pass out of the segments 126 during the insertion procedure. The lead assembly 100 also includes a handle (not shown) similar to the handle 30 discussed above in connection with FIGS. 1–4.

The lead of FIG. 5 is an endocardial lead which is installed by first passing the distal end of the lead assembly 100 through an appropriate blood vessel in the conventional manner so as to gain access to the desired portion of the interior of the heart. Once the electrode tip 105 is in the vicinity of its final attachment point inside the heart, the tip shield 124 is withdrawn by sliding it over the lead insertion device 120. During the withdrawal of the tip shield 124 the segments 126 open, allowing the entire tip shield 124 to be removed from the vicinity of the electrode tip 105.

Once the electrode tip 105 has been exposed, the lead assembly 100 is used in a manner similar to that of the lead assembly 10 of FIGS. 1–4. In particular, the surgeon positions the electrode tip 105 adjacent the selected portion of the heart, withdraws the handle (not shown) with respect to the lead insertion device 120 in order to stretch the coil spring 104, the braid sheath 110 and the insulating sheath 116, and then sharply and abruptly releases the handle (not shown) such that the electrode tip 105 is accelerated toward the interior surface of the heart with sufficient momentum to embed the electrode tip 105 in the heart. In this case, the coil spring 104 is not twisted as it is elongated and therefore no angular momentum is imparted to the electrode tip 105 as it is propelled towards the heart.

Once the electrode tip 105 has been embedded in the heart, installation of the lead 102 is completed by rotating the flange 106 to complete the insertion of the electrode tip 105 and mechanically to engage the prongs 107 in the heart. This rotation is performed by rotating the braid sheath 110 after the liner 118 and the lead insertion device 120 have been removed as described above. The braid sheath 110 efficiently transmits torque along the length of the lead 102 to the flange 106, thereby allowing remote rotation of the flange 106 and electrode tip 105 as necessary either to screw the prongs 107 into the heart, or alternately to unscrew the prongs 107 and electrode tip 105 from the heart. Preferably, the braid sheath 110 is provided with adequate length to accommodate the requisite stretching of the coil spring 104 to propel the electrode tip 105 into the heart as described above. The braid sheath 110 is particularly advantageous in that it allows remote removal of the electrode tip 105 merely by rotating the proximal end of the braid sheath 110, and thereby rotating the flange 106, the prongs 107 and the electrode tip 105 in the appropriate direction.

From the foregong, it should be apparent that a novel method for installing cardiac leads has been described which provides significant advantages in terms of precise lead placement, reduced laceration of the heart, and increased ease of removal of the lead. In addition, improved leads and lead assemblies have been described to carry out this novel method of installation. Furthermore, improved leads have been described which provide improved transmission of torque from the proximal to the distal end of the leads.

Of course, it should be understood that various changes and modifications can be made to the preferred embodiments described in detail above. For example, the torque transmitting braided sheath can be used in connection with conventional leads which are not installed using the novel installation method described above. In addition, such torque transmitting sheaths can be made according to this invention using concentric layers of helical filaments having opposed twists, rather than braided filaments as described above. Furthermore, it should be understood that the installation method of this invention can be practiced in connection with lead assemblies having biasing members included in the insertion device to accelerate the electrode tip towards the heart, rather than using a biasing member such as a coil spring which forms an integral part of the lead itself. In addition, the method and apparatus of this invention can be embodied in installation techniques which use pre-cocked devices for accelerating the lead towards the heart rather than devices of the type described above which require the surgeon manually to cock the insertion device immediately prior to use. Moreover, the novel method of this invention is not limited in all respects to screw-in electrode leads, but can also be used with other types of embedded leads, and the prongs 46 may not be needed in all applications. It is therefore intended that the foregoing detailed description be taken as illustrative of the presently preferred embodiments rather than as limiting the scope of the invention, and that the scope of this invention be defined by the following claims, including all equivalents.

We claim:

1. A method for attaching an electrical lead to a heart comprising the following steps:
    providing a cardiac lead assembly which comprises an elongated cardiac lead, with an exposed electrically conductive electrode tip, projecting axially from the one end of the cardiac lead that serves as an attachment end, and a lead insertion device for holding the cardiac lead;
    pointing the electrode tip at a selected portion of a heart but spaced from the heart; and then
    accelerating the electrode tip, at its position spaced from the heart, as a projectile pointed toward the heart and away from the lead insertion device to provide the electrode tip with a momentum sufficient to cause the electrode tip to penetrate a surface of the heart, thereby embedding the electrode tip in the heart.

2. The invention of claim 1 wherein the electrode tip is a screw-in electrode tip and the acceleration step imparts an angular momentum to the cardiac lead and the electrode tip, which angular momentum tends to screw the screw-in electrode tip into the heart.

3. A method for attaching an electrical lead to a heart comprising the following steps:
    providing a cardiac lead assembly which comprises an elongated cardiac lead, with an exposed electrically conductive electrode tip, projecting axially from one end of the cardiac lead, to serve as an attachment end, a biasing member coupled to the electrode tip, and a lead insertion device for holding the cardiac lead;
    selectively moving the biasing member with respect to the insertion device into a biased position, thereby storing potential energy in the biasing member;
    pointing the electrode tip at a selected portion of the heart, but spaced from said selected heart portion; and
    releasing the biasing member from the biased position to allow the biasing member to accelerate the electrode tip as a projectile, toward the heart and away from the insertion device, and so as to provide the electrode tip with a momentum sufficient to cause the electrode tip to penetrate a surface of the heart, thereby embedding the electrode tip in the heart.

4. The invention of claim 3, wherein the electrode tip is a screw-in tip and the biasing member operates to impart an angular momentum to the cardiac lead and the electrode tip, which angular momentum tends to screw the screw-in electrode tip into the heart.

5. A method for attaching an electrical lead to a heart comprising the following steps:
    providing a cardiac lead assembly which comprises a cardiac lead, a coil spring included in the lead, a screw-in electrode tip secured to the coil spring, and a tubular insertion device disposed about the lead;
    extending the coil spring against the insertion device into an extended position, thereby storing potential energy in the coil spring and urging the electrode tip toward the insertion device;
    pointing the electrode tip at a portion of a heart; and then
    releasing the coil spring from the extended position, thereby propelling the electrode tip toward the heart and away from the insertion device to provide the electrode tip with a momentum sufficient to cause the electrode tip to penetrate a surface of the heart, thereby embedding the electrode tip in the heart.

6. The invention of claim 5 wherein the coil spring operates to impart an angular momentum to the electrode tip, which angular momentum tends to screw the screw-in electrode tip into the heart.

7. The invention of claim 1 or 3 or 5 wherein the portion of the heart is located on an exterior surface of the heart and the cardiac lead is an epicardial lead.

8. The invention of claim 1 or 3 or 5 wherein the portion of the heart is located on an interior surface of the heart and the cardiac lead is an endocardial lead.

9. A cardiac lead assembly comprising:
    an axially elongated electrical lead;
    an electrically conductive electrode tip, included in the lead and positioned to extend away from one end of the lead; and
    means for simultaneously accelerating, as a projectile, the electrical lead and the electrode tip both axially of and angularly about the longitudinal axis of the electrode lead, toward a portion of the heart that is spaced from the electrode tip, with a momentum sufficient to cause the electrode tip to penetrate a surface of a heart, thereby embedding the electrode tip in the heart.

10. The invention of claim 9 wherein the electrode tip is a screw-in electrode tip and the accelerating means includes means for imparting an angular momentum to the electrode tip, which angular momentum tends to screw the screw-in electrode tip into the heart.

11. The invention of claim 9 wherein said electrical lead further comprises an annular metal flange concentric about the axis of the lead and its electrode tip, and being secured adjacent to and surrounding but spaced from the electrode tip such that the tip extends axially outwardly relative to the flange, and with the metal flange being electrically insulated from the electrode tip and from the electrical lead.

12. The invention of claim 11 wherein the annular flange defines at least one elongated prong positioned on the flange, and adapted to penetrate and mechanically engage and grip the heart when the lead is selectively manually rotated about its axis, thereby securing the flange and the lead to the heart.

13. The invention of claim 12 wherein said at least one prong comprises two prongs, wherein each of the prongs is oriented in a spiral axial pattern relative to the annular flange such that the prongs cooperate to urge respective portions of the heart toward the lead tip.

14. The invention of claim 9 wherein the accelerating means comprises a tubular structure positioned around the lead, wherein the electrode tip comprises a screw-in electrode tip, and wherein the lead assembly further comprises means for transmitting torque from the tubular structure to the screw-in electrode tip.

15. The invention of claim 9, wherein the accelerating means comprises:
a tubular structure positioned around a portion of the lead and providing abutment means thereon for cooperation with the lead for limiting axial and rotational movement of the lead relative to the tubular structure;
a coil spring, included in the lead and extending along the length of the lead; and a handle operatively associated with the coil spring for selectively potentiating the coil spring of the lead against the abutment means on the tubular structure.

16. The invention of claim 15 wherein the lead further comprises a transverse flange secured to the coil spring of the lead adjacent the electrode tip, and one end of the tubular structure being adapted to bear against the transverse flange.

17. A cardiac lead assembly comprising:
an electrical lead having a tip end and a proximal end;
an exposed electrode tip included in said lead and positioned to extend away from the tip end of said lead;
a lead insertion device including holding means for releasably manually holding and pointing the tip end of said lead at a selected portion of a body, spaced from the tip end of said lead, and into which the electrode tip is to be implanted; and
resilient biasing means included in said lead and constructed and oriented to normally resist movement of the proximal end of said lead away from the holding means;
said biasing means acting to store potential energy when the proximal end of said lead is moved away from the holding means and held so as to stress the biasing means, and then to impart sufficient projectile momentum to the tip end of said lead, when the proximal end of the biasing means is released from being held in its stressed position, to cause the electrode tip to be projected against and to penetrate a surface of a heart, thereby embedding the electrode tip in the heart; and handle means operatively associated with the biasing member for manually selectively moving the proximal end of the biasing member in an axial direction away from the holding means.

18. The invention of claim 17 wherein the means for manually holding and pointing the tip end of the lead comprises a tubular structure disposed around the lead.

19. The invention of claim 18 wherein a portion of the lead is resiliently elongatable and the biasing member comprises a coil spring included in the lead and normally oriented to resist resilient elongation of the lead.

20. The invention of claim 19 wherein the lead further comprises a flange adjacent the tip end of the lead and the holding means comprises a tubular structure disposed around the lead such that the flange is positioned to normally bear against the tubular structure when the coil spring is elongated by the handle means.

21. The invention of claim 17 wherein the electrode tip comprises a helical screw-in electrode tip and the biasing member is adapted to impart an angular momentum to the tip, which angular momentum tends to screw the screw-in electrode tip into the heart.

22. The invention of claim 17 wherein the electrode tip comprises a screw-in electrode tip and the lead insertion device comprises key means for locking the screw-in electrode tip against rotation with respect to the lead insertion device.

23. A cardiac lead comprising:
an electrode tip;
an elongatable coil spring electrically connected to the tip to form an electrical conductor extending away from the tip;
an elongatable insulating sheath disposed around the coil spring;
said coil spring and sheath cooperating to form an elongatable lead having a spring constant within a selected range, such that the lead can be selectively manually manipulated to cause the coil spring to impart a momentum to the tip sufficient to embed the tip in a heart.

24. The invention of claim 23 further comprising a tubular tip shield positioned removably around the insulating sheath and the electrode tip, said tip shield defining a plurality of flexible segments having a rest, closed position in which the segments substantially surround the electrode tip, and an open position in which the segments expose the electrode tip such that the lead can be passed through a blood vessel with the segments in the closed position, thereby substantially preventing the electrode tip from snagging on the blood vessel, and the tip shield can then be selectively withdrawn, thereby moving the segments to expose the electrode tip.

25. A cardiac lead assembly comprising:
an electrode tip;
an elongatable coil spring electrically connected to the tip to form an electrical conductor extending away from the tip;
an elongatable insulating sheath disposed around the coil spring;

a tubular lead insertion device slidably disposed around the elongatable sheath;

said coil spring and sheath cooperating to form an elongatable lead having a spring constant within a selected range, such that the lead can be selectively manually stretched axially against the insertion device and then released to cause the coil spring to impart a momentum to the tip sufficient to embed the tip in a heart.

26. The invention of claim 25 wherein the electrode tip comprises a screw-in electrode tip, and the lead further includes means for locking the screw-in electrode tip against rotation with respect to the lead insertion device.

27. The invention of claim 25 further comprising a tubular tip shield positioned removably around the lead insertion device and the electrode tip, said tip shield defining a plurality of flexible segments having a rest, closed position in which the segments substantially surround the electrode tip in an open position in which the segments expose the electrode tip such that the lead can be passed through a blood vessel with the segments in the closed position, thereby substantially preventing the electrode tip from snagging on the blood vessel, and the tip shield can then be withdrawn, thereby moving the segments to expose the electrode tip.

28. The invention of claim 23 or 25 wherein the electrode tip comprises a screw-in electrode tip.

29. The invention of claim 23 or 25 wherein the lead further comprises a transverse attachment flange secured to the coil spring and adjacent the electrode tip such that the electrode tip extends axially beyond the most distal surface of the flange.

30. The invention of claim 29 wherein the attachment flange includes a plurality of elongated prongs positioned on the flange space radially outwardly of the electrode tip and adapted to penetrate and mechanically engage the heart, thereby securing the flange to the heart.

31. The invention of claim 30 wherein each of the prongs extends, from its connection to the flange, radially spirally outwardly away from the electrode tip.

32. A cardiac lead comprising:
a screw-in electrode tip;
a flexible conductor connected to the electrode tip to extend away from the tip;
a flexible torque transmitting structure disposed around the flexible conductor, said structure comprising:
a first plurality of flexible filaments disposed in a helical pattern around the flexible conductor, each of said first plurality of flexible filaments defining respective proximal and distal ends;
a second plurality of flexible filaments disposed in a helical pattern around the flexible conductor, each of the second plurality of flexible filaments defining respective proximal and distal ends, the helical pattern of the first plurality of flexible filaments being reversed with respect to the helical pattern of the second plurality of flexible filaments such that the first plurality of flexible filaments repeatedly crosses the second plurality of flexible filaments; and
means for locking the electrode tip against rotation with respect to the distal ends of the first and second pluralities of flexible filaments.

33. The invention of claim 32 further comprising a flexible insulator sheath disposed over the torque transmitting structure.

34. The invention of claim 32 wherein the first and second pluralities of flexible filaments are included in a braided cable.

35. The invention of claim 34 wherein the flexible filaments are formed of a metal.

36. In a method for attaching an elongated electrical lead to a portion of a living body, such as the heart, where the electrical lead is an elongated flexible body having a proximal end and a distal end, with portions of the flexible body defined by coil spring means that serves as a flexible, but shape sustaining, electrical lead body, and which includes an exposed, spread coil, helical electrode tip segment at the lead's distal end, said electrode tip segment being spaced by a transverse rigidifying flange from the flexible, shape sustaining electrical lead body, the spread coil tip being adapted to effect a screw-in of the electrode tip into a portion of a living body; and wherein a portion of the elongated lead body is surrounded by tubular handle means which provides means for holding and pointing the lead's distal end in alignment with, and closely spaced from, that portion of the living body wall which is to have the spread coil helical electrode tip screwed thereinto;

the improvement in the method comprising, in combination:
gaining access to a selected surfact of the living body that is to receive the screw-in electrode tip;
holding the handle means while aiming the screw-in electrode tip toward the selected surface of the living body to be pierced by the electrode tip;
using manually graspable means to elongate a portion of the coil spring that extends between said transverse rigidifying flange and the proximal end of the elongated lead body, to develop a projecting, restoring, force within the elongated lead body;
and suddenly releasing the elongated coil spring to cause the developed projecting force to operate to accelerate the exposed spread coil, helical electrode tip, toward the selected living body wall portion and to effect penetration of said selected wall portion of the living body, and embedding at least a portion of the exposed spread coil electrode tip in said selected wall portion of the living body.

37. The improved method as in claim 36 wherein the portion of the coil spring that is elongated by the manually graspable means is also twisted about the longitudinal axis of the coil spring to also potentialize an angular restoring force in the coil spring, so that, upon release of the manually graspable means, the screw-in electrode tip has imparted thereto a helical acceleration, having both an axial component and an angular component, which operates to cause the screw-in electrical tip to be projected with both angular and axial momentum that causes the screw-in electrical tip to screw itself into the selected area of the living body.

38. A means for implanting a cardiac lead assembly comprising, in combination:
an elongated, electrically conductive, resilient and axially extensible cardiac lead member having a proximal end and a distal end; transverse flange means secured to said elongated member between its ends and adjacent to, but not at, the distal end of said elongated electrically conductive member;
means electrically isolating the exterior axial length of said conductive, resilient member, from adjacent its proximal end to said transverse flange means, and also electrically isolating all surfaces of the transverse flange, from inadvertently delivering electrical energy therefrom to the surrounding environment;

a portion of the elongated, electrically conductive, resilient member extending distally past the isolated transverse flange means to provide an exposed, electrically conductive, implantable electrode tip adapted to be implanted in cardiac tissue;

an annular attachment disc located on the distal side of the transverse flange means, positioned to surround and be spaced from said implantable electrode tip, and being electrically isolated from all portions of the cardiac lead, the axial length of the implantable electrode tip being greater than the axial length of said annular attachment disc;

and implanting means for the cardiac lead assembly comprising an elongated tubular insertion device having proximal and distal ends and being located between the transverse flange means and the proximal end of the axially extensible lead member, and with said elongated electrically isolated member slidably extending axially therethrough, with the proximal end of the cardiac lead projecting forwardly of the insertion device, and with the distal end of the insertion device being adapted to, and being of a size to, abut the electrically isolated transverse flange; by means between the insertion device and transverse flange for separable interengagement for preventing relative rotation between the cardiac lead and the insertion device; a handle means, carried on a portion of the resilient and axially extensible conductive member that projects toward the proximal end of the cardiac lead and beyond the proximal end of the tubular insertion device, for manually axially stretching, and also providing for rotatably twisting, the conductive member to store resilient forces therein, when the insertion device is held abutting, and keyed to, the transverse flange; and the release of the stretched and/or rotated handle means being operative to project the implantable electrode tip in a distal direction away from the manually held insertion device.

* * * * *